US00RE47316E

(19) United States
(12) Reissued Patent
Lehtola et al.

(10) Patent Number: US RE47,316 E
(45) Date of Reissued Patent: Mar. 26, 2019

(54) ORAL FORMULATIONS OF OSPEMIFENE

(71) Applicant: Hormos Medical Ltd., Turku (FI)

(72) Inventors: Veli-Matti Lehtola, Turku (FI); Markku Anttila, Pajulantie (FI)

(73) Assignee: QUATRX PHARMACEUTICALS COMPANY, Ann Arbor, MI (US)

(21) Appl. No.: 15/191,316

(22) Filed: Jun. 23, 2016

Related U.S. Patent Documents

Reissue of:
(64) Patent No.: 8,758,821
Issued: Jun. 24, 2014
Appl. No.: 11/592,989
Filed: Nov. 6, 2006

U.S. Applications:
(63) Continuation of application No. PCT/FI2005/000131, filed on Mar. 2, 2005.

(60) Provisional application No. 60/567,525, filed on May 4, 2004.

(51) Int. Cl.

| | |
|---|---|
| ***A61K 9/14*** | (2006.01) |
| ***A61K 9/48*** | (2006.01) |
| ***A61K 9/20*** | (2006.01) |
| ***A61K 47/10*** | (2017.01) |
| ***A61K 31/075*** | (2006.01) |
| ***A61K 9/08*** | (2006.01) |

(52) U.S. Cl.
CPC ..... *A61K 9/4825* (2013.01); *A61K 9/08* (2013.01); *A61K 9/20* (2013.01); *A61K 31/075* (2013.01); *A61K 47/10* (2013.01)

(58) Field of Classification Search
CPC ..... A61K 9/4825
See application file for complete search history.

(56) References Cited

U.S. PATENT DOCUMENTS

| | | | | |
|---|---|---|---|---|
| 4,117,121 | A | 9/1978 | Gallo-Torres | |
| 5,567,714 | A | 10/1996 | Bruns | |
| 5,597,582 | A * | 1/1997 | Brown et al. | 424/456 |
| 5,912,273 | A | 6/1999 | Degregorio et al. | |
| 6,015,544 | A * | 1/2000 | Foged et al. | 424/1.85 |
| 6,037,379 | A | 3/2000 | Härkönen et al. | |
| 6,245,352 | B1 | 6/2001 | Arbuthnot et al. | |
| 6,245,819 | B1 | 6/2001 | Halonen et al. | |
| 6,525,084 | B2 | 2/2003 | Rasmussen et al. | |
| 6,537,561 | B1 | 3/2003 | Fukui et al. | |
| 6,984,665 | B2 | 1/2006 | Blom et al. | |
| 2003/0036566 | A1 * | 2/2003 | Blom et al. | 514/721 |
| 2003/0083228 | A1 * | 5/2003 | Carpino et al. | 514/1 |
| 2003/0162761 | A1 | 8/2003 | Steiner et al. | |
| 2005/0182143 | A1 | 8/2005 | Anttila | |
| 2005/0187301 | A1 | 8/2005 | Lehtola et al. | |
| 2005/0215528 | A1 | 9/2005 | Furuya et al. | |
| 2005/0227947 | A1 * | 10/2005 | Chen et al. | 514/79 |
| 2006/0105045 | A1 * | 5/2006 | Buchanan et al. | 424/486 |
| 2007/0066536 | A1 * | 3/2007 | Garnick | 514/15 |

FOREIGN PATENT DOCUMENTS

| | | | |
|---|---|---|---|
| CA | 2458452 | A1 | 2/2003 |
| CN | 146085 | A | 10/2003 |
| EP | 0760651 | B1 | 7/2001 |
| EP | 1713458 | B1 | 3/2008 |
| EP | 1718288 | B1 | 4/2011 |
| JP | 6-16556 | A | 1/1994 |
| JP | 7-165610 | | 6/1995 |
| JP | 7-196483 | | 8/1995 |
| JP | 2004-504345 | A | 2/2004 |
| WO | WO 95/24893 | A1 | 9/1995 |
| WO | WO 96/03113 | A1 | 2/1996 |
| WO | WO 96/07402 | A1 | 3/1996 |
| WO | WO 97/32574 | A1 | 9/1997 |
| WO | WO 98/37869 | | 9/1998 |

(Continued)

OTHER PUBLICATIONS

Anttila, M., "Effect of food on the pharmacokinetics of toremifene," *European Journal of Cancer,* 33(Suppl. 8):1144 (1997).

Barth, A., et al., "Influence of Subchronic Administration of Oestradiol, Ethinyloestradiol and Oestradiol Suphamate on Bile Flow, Bile Acid Exretion, and Liver and Biliary Glutathione Status in Rats", *Arch Toxicol.,* 71(7):443-449 (1997).

BI Dianzhous, English translation of Chinese Textbook cited by the examiner, *Pharmaceutics,* 4th ed., People's Medical Publishing House (2003).

Bolhuis, G.K., et al., "Improvement of dissolution of poorly soluble drugs by solid deposition on a super disintegrant. II. The choice of super disintegrants and effect of granulation," *European Journal of Pharmaceutical Sciences,* 63-69, Elsevier Science B.V. (1997).

(Continued)

*Primary Examiner* — Johnny F Railey, II
(74) *Attorney, Agent, or Firm* — Brinks Gilson & Lione; Ryan L. Marshall; William Boudreaux

(57) ABSTRACT

This invention relates to a liquid or semisolid oral drug formulation comprising a therapeutically active compound of the formula (I)

(I)

or a geometric isomer, a stereoisomer, a pharmaceutically acceptable salt, an ester thereof or a metabolite thereof, in combination with a pharmaceutically acceptable carrier.

45 Claims, 1 Drawing Sheet

(56) References Cited

FOREIGN PATENT DOCUMENTS

| | | |
|---|---|---|
| WO | WO 02/07718 A1 | 1/2002 |
| WO | WO 02/056866 A1 | 7/2002 |
| WO | WO 03/103649 | 12/2003 |

OTHER PUBLICATIONS

Chueschov, English translation of "Industrial technology of drugs," 353-355 (1999).
European Patent Office Examination Reports for Application No. 05717258.7 (PCT/FI2005/000131), dated May 5, 2009.
European Patent Office Examination Reports for Application No. 05717258.7 (PCT/FI2005/000131), dated Nov. 9, 2007.
International Preliminary Report on Patentability and Written Opinion for PCT/FI2005/000037, dated May 23, 2006 (received Jun. 13, 2006).
International Preliminary Report on Patentability and Written Opinion for PCT/FI2005/000131, dated Nov. 7, 2006.
Jordan, V.C., "Antiestrogens and Selective Estrogen Receptor Modulators ad Multifunctional Medicines, 2. Clinical Considerations and New Agents," *Journal of Medicinal Chemistry,* 46(7):1081-1111 (Mar. 27, 2003).
Kangas, L., "Biochemical and pharmacological effects of toremifene metabolites," *Cancer Chemotherapy and Pharmacology,* 27:8-12 (1990).
Karlsson, M. O., et al., "Pharmacokinetics of Oral Noscapine", *Eur J Clin Pharmacol.,* 39(3):275-279 (1990).
Kauffman, RF, et al., "Selective Estrogen Receptor Modulators," *Drug News Perspect,* 8:531-539 (1995).
Laight, S.J., et al., "Comparative evaluation of two aspirin formulation techniques," www.ru.ac.za/academic/departments/pharmacy/jrats/vol1_1/poster5/tablet2.html, printed Dec. 3, 2017; 1-6.
Odeku, Oluwatoyin A., et al., "Effects of the method of preparation on the compression, mechanical, and release properties of Khaya gum matrices," *Pharmaceutical Development and Technology,* 11(4):435-441 (2006).
Office Action with English translation for Chinese Application No. 200580004972.7 (PCT/FI2005/000037), dated Jan. 9, 2009.
Office Action with English translation for Russian Application No. 2006133902, dated Jan. 26, 2009.
Office Action with English translation for Russian Application No. 2006133902, dated Dec. 14, 2009.
Porter, Christopher J. H., et al., "Lipid Based Formulations for Oral Administration," *J. of Receptor & Signal Transduction Research,* 21(2&3):215-257 (2001).
Rudnic, E.M., "Oral Solid Dosage Forms," *Remington: The Science and Practice of Pharmacy,* Gennaro, A.R., editor, 20$^{th}$ Ed. Chapter 45, pp. 858-871.
Seki, T., "Basics of Pharmaceutical Treatment", *Clinical Nutrition,* 101(1):26-31 (Jul. 2002).
Singh, Quinton, et al., "Comparative Evaluations of Tablet Formulations," Rhodes University, School of Pharmaceutical Sciences, Department of Pharmaceutics, Rhodes University, Grahamstown, 6140, RSA, www.ru.ac.za/academic/departments/pharmacy/jrats/vol1_1/poster6/tablets8.html, printed Dec. 3, 2017; 1-6.
Skinner, M. And Kanfer, I., "Comparative Bioavailability of Josamycin, a Macrolide Antibiotic, from a Tablet and Solution and the Influence of Dissolution on in Vivo Release", *Biopharm Drug Dispos.,* 19(1):21-29 (Jan. 1998).
Voipio, S.K., et al. "Effects of ospemifene (FC-1271a) on uterine endometrium, vaginal maturation index, and hormonal status in healthy postmenopausal women," *Maturitas,* 43:207-214 (2002).
Raymond F. Kauffman, et al., "Selective Estrogen Receptor Modulators," Drug News & Perspectives 1995 8 (9) pp. 531-539.
Christopher J. H. Porter, et al., "Lipid Based Formulations for Oral Administration," Journal of Receptor & Signal Transduction Research, 21 (2&3) 215-257 (2001).
Chueschov, "Industrial technology of drugs," 353-355 (1999). (with translation).
Bi Dianzhou, Chinese Textbook, Pharmaceutics, Fourth Edition (2003), People's Medical Publishing House (with translation).
International Preliminary Report on Patentability and Written Opinion for PCT/FI2005/000037, dated May 23, 2006.
European Patent Office Examination Reports for Application No. 05 708 125.9 (PCT/FI2005/000037). dated Sep. 26, 2008.
European Patent Office Examination Reports for Application No. 05 708 125.9 (PCT/FI2005/000037), dated Mar. 25, 2008.
European Patent Office Examination Reports for Application No. 05 708 125.9 (PCT/FI2005/000037), dated Jul. 20, 2007.
European Patent Office Examination Reports for Application No. 05 717 258.7 (PCT/2005/000131), dated May 5, 2009.
European Patent Office Examination Reports for Application No. 05 717 258.7 (PCT/2005/000131), dated Nov. 9, 2007.
Jordan, V. Craig, "*Antiestrogens and Select Estrogen Receptor Modulators as Multifunctional Medicines, 2. Clinical Considerations and New Agents,*"Journal of Medicinal Chemistry, vol. 46, No. 7, Mar. 27, 2003, pp. 1081-1111.
Rudnic, E.M., "*Oral Solid Dosage Forms*", Remington: The Science and Practice of Pharmacy, Gennaro, A.R., editor, 20$^{th}$ Ed. Chapter 45, pp. 858-871, dated Dec. 15, 2000.
G.K. Bolhuis, K. Zuurman, G.H.P. te Wierik; *Improvement of dissolution of poorly soluble drugs by solid deposition on a super disintegant. II. The choice of super disintegrants and effect of granulation;* European Journal of Pharmaceutical Sciences; 1997; 63-69; Elsevier Science B.V.
Quinton Singh, Hiren Patel, Mohamed Cassim; *Comparative Evaluations of Tablet Formulations;* Rhodes University, School of Pharmaceutical Sciences, Department of Pharmaceutics, Rhodes University, Grahamstown, 6140, RSA; www.ru.ac.za/academic/departments/pharmacy/jrats/vol1_1/poster6/tablet8.html; printed Dec. 3, 2007; 1-6.
Patent Office of the Russian Federation, Official Action for Application No. 2006133902 with English translation, dated Jan. 26, 2009.
Patent Office of the Russian Federation, Official Action for Application No. 2006133902 with English translation, dated Dec. 14, 2009.
Chinese Patent Office, Office Action for Application No. 200580004972.7 (PCT/FI2005/000037) with English translation, dated Jan. 9, 2009.
International Search Report of PCT/FI2005/000131, dated Jun. 20, 2005.
International Search Report of PCT/FI2005/000037, dated May 24, 2005.
Bartha, A., et al., "Influence of Subchronic Administration of Oestradiol, Ethinyloestradiol and Oestradiol Suphamate on Bile Flow, Bile Acid Exretion, and Liver and Biliary Glutathione Status in Rats", *Arch Toxicol.,* vol. 71, No. 7, pp. 443-449, 1997.
*Basic Course in Pharmaceutical Development IX No. 15, Pharmaceutical Design Method* (1), pp. 8, Chijin Shokan, Jun. 28, 1975.
Decision of Rejection from corresponding Japanese Application No. 2012-105131, dated Jan. 10, 2012, 10 pages.
*New Theories of Pharmacology:* Third Edition, pp. 19, Nankodo Press, Apr. 10, 1987.

* cited by examiner

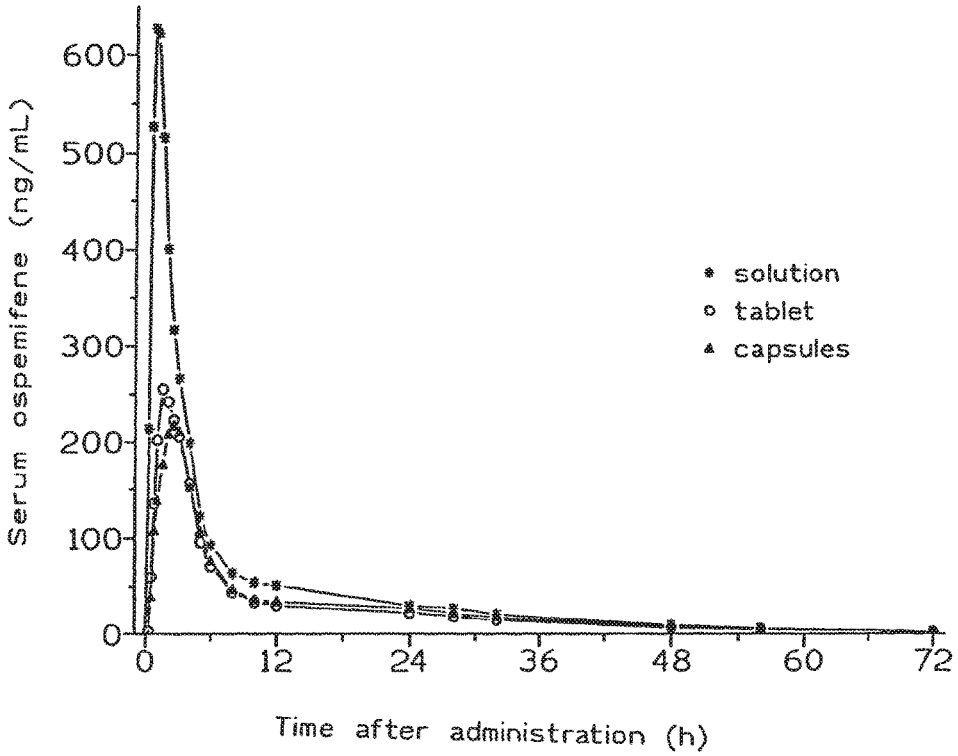
Serum ospemifene (ng/mL)
600
500
400
300
200
100
0
0
12
24
36
48
60
72
Time after administration (h)
solution
tablet
capsules

ORAL FORMULATIONS OF OSPEMIFENE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application is a continuation of PCT/FI05/000131, filed Mar. 2, 2005, which claims priority to U.S. provisional application No. 60/567,525 filed May 4, 2004, both of which are incorporated herein by reference.

BACKGROUND OF THE INVENTION

1. Field of the Invention

This invention relates to a liquid or semisolid oral drug formulation comprising ospemifene or a closely related compound as active ingredient.

2. Background of the Invention

The publications and other materials used herein to illuminate the background of the invention, and in particular, cases to provide additional details respecting the practice, are incorporated by reference.

"SERM"s (selective estrogen receptor modulators) have both estrogen-like and antiestrogenic properties (Kauffman & Bryant, 1995). The effects may be tissue-specific as in the case of tamoxifen and toremifene which have estrogen-like effects in the bone, partial estrogen-like effect in the uterus and liver, and pure antiestrogenic effect in breast cancer. Raloxifene and droloxifen are similar to tamoxifen and toremifene, except that their antiestrogenic properties dominate. Based on the published information, many SERMs are more likely to cause menopausal symptoms than to prevent them. They have, however, other important benefits in elderly women: they decrease total and LDL cholesterol, thus diminishing the risk of cardiovascular diseases, and they may prevent osteoporosis and inhibit breast cancer growth in post-menopausal women. There are also almost pure antiestrogens under development Ospemifene is the Z-isomer of the compound of formula (I)

(I)

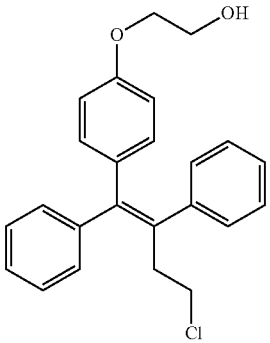

and it is one of the main metabolites of toremifene, is known to be an estrogen agonist and antagonist (Kangas, 1990; International patent publications WO 96/07402 and WO 97/32574). The compound is also called (deaminohydroxy) toremifene and it is also known under the code FC-1271a.

Ospemifene has relatively weak estrogenic and antiestrogenic effects in the classical hormonal tests (Kangas, 1990). It has anti-osteoporosis actions and it decreases total and LDL cholesterol levels in both experimental models and in human volunteers (International patent publications WO 96/07402 and WO 97/32574). It also has antitumor activity in an early stage of breast cancer development in an animal breast cancer model. Ospemifene is also the first SERM which has been shown to have beneficial effects in climacteric syndromes in healthy women. The use of ospemifene for the treatment of certain climacteric disorders in post-menopausal women, namely vaginal dryness and sexual dysfunction, is disclosed in WO 02/07718. The published patent application WO 03/103649 describes the use of ospemifene for inhibition of atrophy and for the treatment or prevention of atrophy-related diseases or disorders in women, especially in women during or after the menopause.

OBJECT AND SUMMARY OF THE INVENTION

An object of the present invention is to provide an improved drug formulation containing ospemifene, where the absorption of the drug is essentially increased and the variability in plasma level is essentially decreased.

Thus, the invention concerns a liquid or semisolid oral drug formulation comprising a therapeutically active compound of the formula (I)

(I)

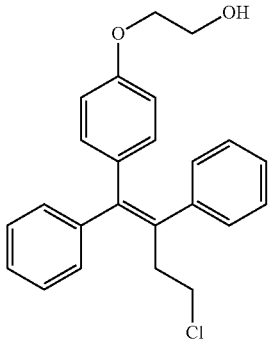

or a geometric isomer, a stereoisomer, a pharmaceutically acceptable salt, an ester thereof or a metabolite thereof, in combination with a pharmaceutically acceptable carrier.

BRIEF DESCRIPTION OF THE DRAWING

FIG. 1 shows serum concentration of ospemifene versus time after a single dose of 60 mg ospemifene administered as a 60 mg tablet (circles), two hard gelatine 30 mg capsules (triangles) or a solution (stars).

DETAILED DESCRIPTION OF THE INVENTION

The term "liquid formulation" refers here particularly to a solution, a suspension with solid particles dispersed in a liquid, an emulsion with liquid droplets dispersed in a liquid, or to a syrup.

The term "semisolid formulation" refers especially to gels and pastes.

According to one preferred embodiment, the liquid drug formulation is a solution of compound I in a suitable carrier, which can be a single carrier or a mixture of several carriers.

The compounds of formula I have very low solubility in water. The carrier shall therefore preferably comprise one or more lipophilic ingredients. In order to achieve enhanced bioavailability it is preferable to use digestible lipids such as triglycerides, diglycerides, fatty acids, phospholipids, or the like instead of indigestible oils such as mineral oils (Porter and Charman, 2001). A special group of useful carriers or ingredients therein may be cholane derivatives. U.S. Pat. No. 4,117,121 disclosed a group of cholane derivatives useful to decrease cholesterol level and to increase bile flow. The bioavailability enhancing ingredients are, however, not restricted to the aforementioned.

According to another preferred embodiment, the liquid drug formulation is a suspension of fine solid particles of the compound I in a liquid. The liquid can be a lipophilic or hydrophilic liquid or a mixture of several liquids. Said liquids can also comprise dissolved ingredients. By decreasing the particle size of the dispersed drug compound, the surface area available for digestion and drug release is enhanced. Preferably at least 90% of the drug substance shall have a particle size less than 150 micrometer, and 50% of the drug substance shall have a particle size less than 25 micrometer. Especially preferably, 90% of the drug substance shall have a particle size less than 50 micrometer, and 50% of the drug substance shall have a particle size less than 15 micrometer.

According to a third preferred embodiment, the liquid formulation is an emulsion. Because the aqueous solubility of compound I is very low, the emulsion is preferably a dispersion of a lipophilic phase (e.g., a solution of compound I in a lipophilic liquid) in an aqueous phase (oil-in-water emulsion). The emulsion may comprise additional components such as stabilizers (surfactants), emulsifiers and thickeners. According to a particularly preferred embodiment, the emulsion is a microemulsion or nanoemulsion. Micro- and nanoemulsions are, in contrast to conventional emulsions, isotropic, transparent and thermodynamically stable. The average size of the dispersed droplets is in a microemulsion typically about 10000 nm or below and in a nanoemulsion 100 nm or below.

According to a fourth preferred embodiment, the liquid formulation is a syrup. Typical examples of semisolid oral formulations are gels and pastes. Gels are created by adding a gelatinizer such as gelatine or a polysaccharide to a solution, suspension or emulsion comprising compound I. According to one preferred embodiment, the gel is created by addition of a gelatinizer to a microemulsion according to EP 760651 B1.

Although the liquid formulations such as solutions, emulsions and suspensions can be packed in larger bottles for many doses, it may be preferable to have the drug formulation packed into a unit dosage form, such as a capsule. Such capsule formulations are called softgel capsules. Soft gelatin capsules (or softgel capsules) consist of a liquid or semisolid matrix inside a one-piece outer shell, such as a gelatin shell. The drug compound itself may be either in solution, suspension or emulsion in the capsule-fill matrix. The characteristics of the fill matrix may be hydrophilic (for example polyethylene glycols) or lipophilic (such as triglyceride vegetable oils), or a mixture of both hydrophilic and lipophilic ingredients.

Significant advances have been made in recent years in the formulation of fill matrices. As examples can be mentioned microemulsions or nanoemulsions of the drug encapsulated as preconcentrates in the capsule. This means that the fill matrix is a concentrated micro- or nanoemulsion, i.e., a combination of a lipophilic liquid containing the hydrophobic drug, a small amount of hydrophilic liquid and a surfactant. After oral administration the microemulsion will become diluted in the gastrointestinal fluid. Alternatively, the matrix may comprise only the ingredients, i.e., the drug, a lipid or a lipid mixture and one or more surfactants. The ingredients will, upon administration, spontaneously create a microemulsion (or nanoemulsion) in the gastrointestinal fluid.

The softgel capsule consists for example of gelatin, water and a plasticizer. It may be transparent or opaque, and can be coloured and flavoured if desired. Preservatives are not required owing to the low water activity in the finished product. The softgel can be coated with enteric-resistant or delayed-release material. Although virtually any shape softgel can be made, oval or oblong shapes are usually selected for oral administration.

The improved drug formulation according to this invention is particularly useful when treating women during or after the menopause. However, the method according to this invention is not restricted to women in this age group.

The term "metabolite" shall be understood to cover any ospemifene or (deaminohydroxy)toremifene metabolite already discovered or to be discovered. As examples of such metabolites can be mentioned the oxidation metabolites mentioned in Kangas (1990) on page 9 (TORE VI, TORE VII, TORE XVIII, TORE VIII, TORE XIII), especially TORE VI and TORE XVIII, and other metabolites of the compound. The most important metabolite of ospemifene is 4-hydroxy-ospemifene, which has the formula

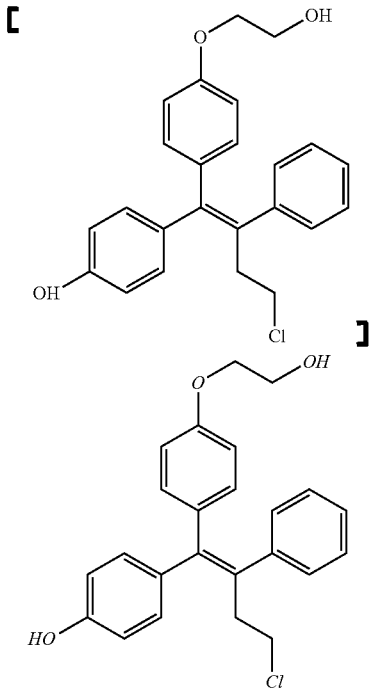

The use of mixtures of isomers of compound (I) shall also be included in this invention.

The compound (I) is preferably ospemifene.

The improved drug formulation according to this invention is useful in any application of ospemifene, especially when the compound is used for treatment or prevention of osteoporosis or for treatment or prevention of symptoms related to skin atrophy, or to epithelial or mucosal atrophy.

A particular form of atrophy which can be inhibited by administering of ospemifene is urogenital atrophy. Symptoms related to urogenital atrophy can be divided in two subgroups: urinary symptoms and vaginal symptoms. As examples of urinary symptoms can be mentioned micturation disorders, dysuria, hematuria, urinary frequency, sensation of urgency, urinary tract infections, urinary tract inflammation, nocturia, urinary incontinence, urge incontinence and involuntary urinary leakage. As examples of vaginal symptoms can be mentioned irritation, itching, burning, malodorous discharge, infection, leukorrhea, vulvar pruritus, feeling of pressure and postcoital bleeding.

According to previous data, the optimal clinical dose of ospemifene is expected to be higher than 25 mg daily and lower than 100 mg daily. A particularly preferable daily dose has been suggested in the range 30 to 90 mg. At the higher doses (100 and 200 mg daily), ospemifene shows properties more similar to those of tamoxifen and toremifene. Due to the enhanced bioavailability according to the method of this invention, it can be predicted that the same therapeutical effect can be achieved with doses lower than those recommended earlier.

The invention will be disclosed more in detail in the following non-restrictive Example.

Example

A clinical study was carried out in order to evaluate the bioavailability of ospemifene given as tablet, hard gelatine capsule and as solution.

Healthy male Caucasian individuals (n=23), age 18 to 35 years, were subjected to 3 different tests in which they were given a) two hard gelatine capsules, each containing 30 mg ospemifene; b) one tablet containing 60 mg ospemifene; or c) 3.7 g of a solution containing 60 mg ospemifene. In c) the solvent was a mixture of ethanol-PEG-propyleneglycol (2,7:1:2,5). The tests were separated from each other by a washout period lasting at least one week. Blood samples for the determination of serum ospemifene concentrations were collected during each test at several time points after administration. Serum ospemifene concentrations were determined using reversed phase HPLC with fluorescence detection after photochemical activation.

The results are shown in FIG. 1, which discloses the mean serum concentration of ospemifene versus time after administration after a single oral dose of 60 mg ospemifene given as two 30 mg hard gelatine capsules (triangles), as one 60 mg tablet (circles) or as a dose of a solution containing 60 mg ospemifene (stars). It can be seen that peak concentrations were much higher after administration of solution (700 ng/mL) than after tablet and hard capsules, which were very similar, 280 and 277 ng/mL, respectively. Accordingly, the AUC-values were substantially higher after solution (approximately 3000 ng h/mL) when compared to the AUC-values of tablets and hard capsules (approximately 2000 ng h/mL). Therefore it can be concluded that the absorption of ospemifene from solution was much faster and the bioavailability much higher than from tablets and hard capsules. Additionally, the variability of the pharmacokinetic parameters decreased.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

What is claimed is:

1. A liquid, oral drug formulation comprising [a therapeutically active compound of the formula (I):

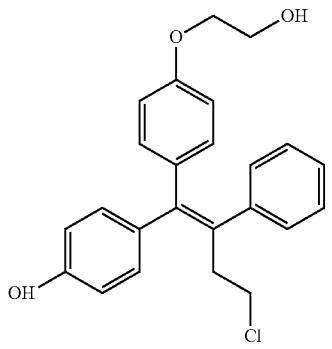

or a geometric isomer, a stereoisomer, a pharmaceutically acceptable salt, an ester thereof or a metabolite thereof,] *ospemifene* in combination with a pharmaceutically acceptable carrier comprising a mixture of ethanol, polyethylene glycol, and propyleneglycol.

[2. The formulation of claim 1, wherein the compound is ospemifene.]

3. The formulation according to claim [2] *1* further comprising a bile-flow promoting agent selected from the group consisting of (a) a pharmaceutically acceptable carrier comprising a digestible lipid selected from the group consisting of a triglyceride, a diglyceride, a fatty acid, or a phospholipid; and (b) a cholane derivative and a pharmaceutically acceptable carrier.

4. The drug formulation according to claim 3 wherein the formulation is a suspension.

5. The drug formulation according to claim [2] *1* wherein the formulation is an emulsion.

6. The drug formulation according to claim [2] *1* wherein the formulation is a microemulsion or nanoemulsion.

7. The drug formulation according to claim 3 wherein the formulation is a syrup.

8. The drug formulation according to claim [2] *1* wherein the formulation is packed into a unit dosage form.

9. The drug formulation according to claim 8 wherein the dosage form is the formulation encapsulated in a soft gel capsule.

10. The drug formulation according to claim [2] *1* wherein the formulation is a solution.

11. The drug formulation according to claim 10 wherein the formulation is packed into a unit dosage form.

12. The drug formulation according to claim 11 wherein the dosage form is the formulation encapsulated in a soft capsule.

13. The drug formulation according to claim 10 wherein the dosage amount is from 30 to 90 mg/day.

14. The drug formulation according to claim 11 wherein the dosage amount is 60 mg.

15. The drug formulation according to claim [2] *1* wherein the dosage amount is from 30 to 90 mg/day.

16. The drug formulation according to claim 15 wherein the dosage amount is 60 mg.

17. The drug formulation according to claim 3 wherein the bile flow promoting agent is a cholane derivative.

18. The drug formulation according to claim 3 wherein the bile flow promoting agent is a digestible lipid.

19. The drug formulation according to claim [2] *1* further comprising ethanol.

20. The drug formulation according to claim 10 further comprising ethanol.

21. A liquid, oral drug formulation consisting essentially of [a therapeutically active compound of the formula (I):

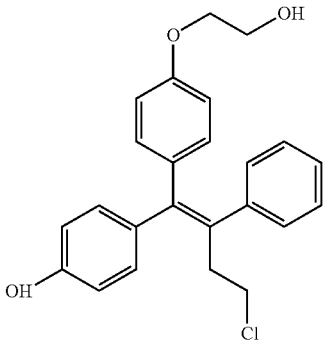

or a geometric isomer, a stereoisomer, a pharmaceutically acceptable salt, an ester thereof or a metabolite thereof, in combination with] *ospemifene and* a pharmaceutically acceptable carrier comprising a mixture of ethanol, polyethylene glycol, and propyleneglycol.

[22. The formulation of claim 21 wherein the compound is ospemifene.]

23. The drug formulation according to claim [22] *21* wherein the formulation is packed into a unit dosage form.

*24. A method of treating a climacteric disorder in a postmenopausal woman, comprising administering a liquid formulation to the postmenopausal woman, the liquid formulation comprising:*

*ospemifene;*

*and a pharmaceutically acceptable, liquid carrier.*

*25. The method of claim 24, wherein the formulation is an emulsion.*

*26. The method of claim 24, wherein the formulation is packed into a unit dosage form.*

*27. The method of claim 24, wherein the pharmaceutically acceptable liquid carrier is a digestible lipid.*

*28. The method of claim 27, wherein the digestible lipid is selected from the group consisting of a triglyceride, a diglyceride, a fatty acid, or a phospholipid.*

*29. The method of claim 24, wherein the liquid formulation further comprises a surfactant.*

*30. The method of claim 24, wherein the climacteric disorder is selected from the group consisting of vaginal dryness and sexual dysfunction.*

*31. The method of claim 30, wherein the climacteric disorder is vaginal dryness.*

*32. The method of claim 30, wherein the climacteric disorder is sexual dysfunction.*

*33. The method of claim 24, wherein the amount of ospemifene present is between 30 to 90 mg.*

*34. A liquid, oral drug formulation comprising ospemifene and a pharmaceutically acceptable, liquid carrier.*

*35. The formulation of claim 34, wherein the pharmaceutically acceptable carrier is a digestible lipid.*

*36. The formulation of claim 35, wherein the formulation is a suspension.*

*37. The formulation of claim 34, wherein the formulation is an emulsion.*

*38. The formulation of claim 34, wherein the formulation is a microemulsion or nanoemulsion.*

*39. The formulation of claim 35, wherein the digestible lipid is selected from the group consisting of a triglyceride, a diglyceride, a fatty acid, or a phospholipid.*

*40. The formulation of claim 34, wherein the formulation is packed into a unit dosage form.*

*41. The formulation of claim 34, wherein the formulation is encapsulated in a soft gel capsule.*

*42. The formulation of claim 34, wherein the amount ospemifene is from 30 to 90 mg.*

*43. The formulation of claim 34, wherein the amount of ospemifene is higher than 25 mg.*

*44. The formulation of claim 35, further comprising a bile flow promoting agent.*

*45. The formulation of claim 39, wherein the bile flow promoting agent is a cholane derivative.*

*46. The formulation of claim 34, wherein the pharmaceutically acceptable carrier comprises a mixture of ethanol, polyethylene glycol, and propyleneglycol.*

*47. The formulation of claim 34, further comprising a surfactant.*

* * * * *